United States Patent [19]
Leupold et al.

[11] Patent Number: 5,082,504
[45] Date of Patent: Jan. 21, 1992

[54] PROCESS FOR THE PREPARATION OF A MIXTURE OF SUCROSE OXIDATION PRODUCTS AND THE USE THEREOF

[75] Inventors: Ernst I. Leupold, Neu-Anspach; Karl-Heinz Schönwälder, Kelkheim; Wolfram Fritsche-Lang, Bensheim; Merten Schlingmann, Konigstein; Adolf Linkies, Frankfurt am Main; Werner Gohla, Niederkassel; Franz-Josef Dany, Erftstadt, all of Fed. Rep. of Germany

[73] Assignee: Hoechst Aktiengesellschaft, Frankfurt am Main, Fed. Rep. of Germany

[21] Appl. No.: 462,489

[22] Filed: Jan. 10, 1990

[30] Foreign Application Priority Data

Jan. 12, 1989 [DE] Fed. Rep. of Germany ....... 3900677

[51] Int. Cl.$^5$ .................................................. B08B 3/00
[52] U.S. Cl. ................................. 134/42; 252/174.17; 252/174.18
[58] Field of Search ..................... 134/42; 252/174.17, 252/174.18

[56] References Cited

FOREIGN PATENT DOCUMENTS

3535720A1  4/1987  Fed. Rep. of Germany .

*Primary Examiner*—Asok Pal
*Attorney, Agent, or Firm*—Finnegan, Henderson, Farabow, Garrett, and Dunner

[57] ABSTRACT

A process for the preparation of a mixture of sucrose oxidation products which contains a salt of sucrosetricarboxylic acid and which is obtained by reaction of sucrose with oxygen in an aqueous medium in the presence of a platinum metal/active carbon catalyst at elevated temperatures and neutralization of the reaction product to convert into the salt form, which comprises the reaction being carried out discontinuously, the starting materials being heated stepwise over the course of several hours from room temperature up to 60° to 95° C. and then the reaction product being isolated where appropriate.

The oxidation products obtained in this way have, in particular, improved washing properties.

21 Claims, No Drawings

PROCESS FOR THE PREPARATION OF A MIXTURE OF SUCROSE OXIDATION PRODUCTS AND THE USE THEREOF

DESCRIPTION

The present invention relates to a process for the preparation of a mixture of sucrose oxidation products which is essentially composed of the sodium salt of sucrosetricarboxylic acid (STA), and to the use thereof, especially as additive in washing agents.

Because of their eutrophic effect on water courses, the use of phosphates in washing and cleaning agents is subject to statutory restriction in a number of countries, and is even banned in some. This is why a large number of substitutes for phosphates, especially for sodium tripolyphosphate, have now been developed and proposed as builders. However, no single substance has yet achieved the totality of desirable washing properties of sodium tripolyphosphate. Only builder combinations are able to replace the phosphates to a first approximation. Only relatively few phosphate substitutes, or more appropriately phosphate partial substitutes, are completely satisfactory in terms of their ecological properties. Even though they do not promote eutrophication of water courses, some of them do behave in the environment in a way which must be regarded as unacceptable, for example the remobilization of heavy metals from the water-course sediments or deficient biodegradability, so that their environmental relevance is uncertain even though they do not, at the present state of knowledge, have to be categorized as toxic at the present time. This is why there is a continuing search for efficient washing agent builders which can be categorized as acceptable in terms of their ecological behavior.

German Offenlegungsschrift 3 535 720 discloses a process for the preparation of sucrosetricarboxylic acid. According to this, sucrose is oxidized with oxygen, where appropriate mixed with inert gases, for example in the form of air, with the aid of a catalyst which is considerably more efficient than platinum/alumina, in an aqueous medium. The sucrosetricarboxylic acid formed in this can in this connection be employed as such or in the form of the directly resulting reaction products, which are, in particular, mixtures of this acid with various mono- and/or dicarboxylic acids as well as byproducts or breakdown products such as, for example, oxalic acid, as builder in washing agent formulations. However, it has emerged that although these products are distinguished by satisfactory ecological behavior, their efficiency in terms of washing behavior is only limited.

It has now been found, surprisingly, that the crude mixture of reaction products obtained by the known process has considerably improved washing properties when the course of the process is modified in a characteristic manner.

Hence the invention relates to a process for the preparation of a mixture of sucrose oxidation products which contains a salt, preferably the sodium salt, of sucrosetricarboxylic acid and which is obtained by reaction of sucrose with oxygen in an aqueous medium in the presence of a platinum metal/active carbon catalyst at elevated temperatures and neutralization of the reaction product to convert into the salt form with, preferably, an alkaline sodium compound, which comprises the reaction being carried out discontinuously, the starting materials being heated stepwise over the course of several hours from room temperature up to 60 to 95° C, preferably 70 to 80° C, and then the reaction product being isolated where appropriate.

The invention also relates to the use of these oxidation products, in particular as additive in washing and cleaning agents.

The process according to the invention is carried out in principle like the process claimed in the said German Offenlegungsschrift 3 535 720, but with the measures evident from the above characterizing features.

Thus, according to the invention, sucrose is oxidized with oxygen, where appropriate mixed with inert gases such as nitrogen, that is to say, for example, in the form of air, in an aqueous medium in the presence of suitable catalysts.

Suitable catalysts are those based on platinum metals, such as osmium, iridium, rhodium, ruthenium, palladium and/or platinum, with platinum being preferred, which are applied to active carbons as support. These catalysts generally contain 5 to 10 % by weight of metal, especially platinum. This oxidation is preferably carried out in such a way that solid catalyst is treated in the aqueous reaction medium with gaseous oxygen, i.e. in a three-phase reaction. In another preferred embodiment, highly concentrated oxygen is used, and the reaction solution is circulated, which may facilitate the establishment and maintenance of the pH.

The process according to the invention is, as a rule, carried out discontinuously, for example in a bubble column reactor. It would also be possible in principle for the reaction to be carried out continuously if a device with several cascades each of increasing temperature is used. However, because of the considerable elaboration of the apparatus, the continuous reaction is far less economic.

In general, the process according to the invention is carried out under atmospheric pressure, but it is also possible to use total pressures up to 100 bar, preferably 10 bar, whereby the supply of oxygen and/or the reaction temperature can be increased. It is advantageous in this connection to maintain defined sucrose concentrations; however, over-oxidation takes place easily below 5 % by weight, and only relatively low conversions can be achieved above 20 % by weight under atmospheric pressure. The pH of the sucrose solution which is to be oxidized is, as a rule, maintained between 5 and 9, preferably between 6 and 8.5 and, in particular, between 7 and 8. This is expediently achieved with an alkaline compound, which is preferably physiologically tolerated, of a metal of the first and second main groups of the periodic table, preferably of an alkali metal such as sodium and/or potassium, in particular sodium. Suitable for this purpose are appropriate buffer substances such as sodium (bi)carbonate or appropriate bases such as sodium hydroxide solution.

The reaction can be carried out in all types of apparatus suitable for carrying out reactions in the liquid phase with or without the application of excess pressure, that is to say, for example, in a jacketed bubble column reactor which contains the suspension of the catalyst in the aqueous medium and has at the bottom a sintered disk or another suitable porous membrane and through which a gas stream which has been extremely finely divided by this partition membrane passes from the underside. For economic reasons, the oxygen is expediently passed through the reaction medium at such a rate that the catalytically activated oxygen has just been consumed at the top end of the bubble column. It may be advantageous to stir the reaction mixture improve the mixing and extend the time the oxygen acts. An example of another suitable apparatus is the trickle phase reactor.

One feature essential to the invention is the specific control of temperature during the oxidation of sucrose, in such a manner that the temperature is increased, continuously or discontinuously, over the course of several hours, preferably 5 to 15, in particular 8 to 12, hours, from room temperature to temperatures of about 60 to 95° C., preferably 70 to 80° C.

In a preferred embodiment, this entails the temperature of the starting materials being raised, starting from a room temperature of, for example, 20° C, over the course of about 5 to 15, preferably of 8 to 12, and in particular, about 10 hours, to about 70 to 80° C. temperature being increased by 0.5 to 3° C, preferably by about 1° C, every 5 to 20, preferably every 8 to 15 and, in particular, every 12 minutes.

The required reaction time is expediently determined by samples of the reaction solution being taken and analyzed at particular time intervals. For example, the yield of reaction products can be determined continuously in a straightforward manner by analyzing a sample by high-pressure liquid chromatography, comparing with standard solutions. It is advisable to optimize the reaction time, because to pass oxygen in for an unnecessarily long time may result in over-oxidation and a reduction in the yield of the desired reaction products.

The resulting reaction solution, which contains the sucrose which has been formed in a mixture with less oxidized precursors and various byproducts or breakdown products, is then subsequently adjusted, for the conversion into the salt form, to a pH of 8 to 10, preferably approximately 9, if the pH is not already at this value after the oxidation. This can take place by adding appropriate amounts of the alkaline compounds described hereinbefore, preferably an alkaline sodium compound such as sodium hydroxide solution or sodium (bi)carbonate.

The mixture of oxidation products obtainable according to the invention is then worked up or isolated from the reaction solution in a known manner, for example by freeze- or spray-drying or by other processes suitable for this purpose. The main component in the solid mixture obtained in this way is the salt of sucrosetricarboxylic acid and it generally accounts for at least 30 % by weight, preferably more than 40 % by weight, of this mixture.

The product isolated in this way is suitable in particular as an additive (builder) in washing or cleaning agent formulations. It can also be employed as additive to foodstuffs, as crosslinker in coating formulations etc.

The examples which follow illustrate the invention.

EXAMPLES

I. Preparation of sucrosetricarboxylic acid 20 l(STP)/h oxygen were passed from below, through sintered glass disk, into an externally heated, vertically arranged glass tube (diameter: 50 mm, length: 800 mm) which had been charged with a mixture of 120 g of sucrose, 1.2 l of water and 50 g of a commercially available catalyst (5 % platinum on active carbon). The initial temperature was 20° C, and this was raised over the course of 10 h by 1° C. every 12 minutes to 70° C. 30 % strength aqueous NaOH was added to maintain the pH of the solution at 8.0 and to adjust it to 9.0 at the end of the reaction. The filtered reaction mixture was spray-dried, yield: 114 g. The content of sucrosetricarboxylic acid in the form of the trisodium salt was 41 % by weight.

II Technical testing of washing agents

The following characteristic data were determined to characterize the reaction products obtainable according to the invention as builder;
Lime-binding capacity: about 40 mg Ca/g
Biodegradability (DIN 38,412/25 static test): >70%
Bacterial toxicity (consumption test): >1,000 mg/l The superiority of the mixture obtained according to the invention as builder is evident from the test results on washing agent formulations in which merely the sucrosetricarboxylic acid obtained as in German Offenlegungsschrift 3 535 720 was replaced by the product according to the invention. These washing agents were technically tested in accordance with the recognized rules of the art based on DIN 44,983:

The cleansing power (reflectance difference) was determined by photometric measurement of the reflectance (Zeiss RFC 3 color-measuring apparatus) on WFK and EMpA test soiled fabric. Used for this was the "difference method" corresponding to the following equation:

$$\% \Delta R = \% R_g - \% R_u$$

$\% \Delta R = \%$ reflectance difference (cleansing power)
$\% R_g = \%$ reflectance of washed fabric
$\% R_u = \%$ reflectance of unwashed fabric The fabric deposition (incrustation) was determined in the form of the inorganic fabric ash as percentage residue on heating at 800° C.

The washing agent powders were produced in some cases by the so-called hot-spray process and in some cases by the so-called spray aerosol mixing process (dry mixing process).

The hot spraying was carried out using a laboratory spray-dryer (Bchi type 190) under the following conditions:

| Inlet temperature | about 180° C. |
| Outlet temperature | about 100° C. |
| Spraying pressure | 5 bar |
| Solids concentration | 30% by weight |

Used for the spray aerosol mixing process was a free-fall mixer, and the liquid ingredients were sprayed using a suitable spraying device. Details of the process are described in "Seifen, Fette, le, achse", Volume 99, No. 13, 1973, pages 351 to 357.

| Washing agent formulations | | | | | |
|---|---|---|---|---|---|
| Spray aerosol mixing process Example | | Hot-spray process Example | | Spray aerosol mixing process Example | |
| 1A | 1B | 2A | 2B | 3A | 3B |
| Tricarboxylic acid (STA) | | | | | |
| STA (known product) 10.0 | — | 10.0 | — | 21.5 | — |
| STA (according to the — | 10.0 | — | 10.0 | — | 21.5 |

-continued

Washing agent formulations

| | Spray aerosol mixing process Example | | Hot-spray process Example | | Spray aerosol mixing process Example | |
|---|---|---|---|---|---|---|
| | 1A | 1B | 2A | 2B | 3A | 3B |
| invention) | | | | | | |
| Zeolite | 21.5 | 21.5 | 21.5 | 21.5 | 10.0 | 10.0 |
| Na perborate tetrahydrate | 20.0 | 20.0 | 20.0 | 20.0 | 20.0 | 20.0 |
| Anionic surfactants | 7.0 | 7.0 | 7.0 | 7.0 | 7.0 | 7.0 |
| Non-ionic surfactants | 4.0 | 4.0 | 4.0 | 4.0 | 4.0 | 4.0 |
| Soap | 3.5 | 3.5 | 3.5 | 3.5 | 3.5 | 3.5 |
| Na silicate | 5.0 | 5.0 | 5.0 | 5.0 | 5.0 | 5.0 |
| Carboxymethylcellulose | 1.0 | 1.0 | 1.0 | 1.0 | 1.0 | 1.0 |
| Methylcellulose | 0.5 | 0.5 | 0.5 | 0.5 | 0.5 | 0.5 | remainder conventional washing agent ingredients to 100%

Washing agent formulations

| | Hot-spray process Example 4 | Spray aerosol mixing process Example 5 |
|---|---|---|
| Tricarboxylic acid (STA) | | |
| STA (known product) | — | — |
| STA (according to the invention) | — | — |
| Zeolite | 10.0 | 21.5 |
| Na perborate tetrahydrate | 20.0 | 20.0 |
| Anionic surfactants | 7.0 | 7.0 |
| Non-ionic surfactants | 4.0 | 4.0 |
| Soap | 3.5 | 3.5 |
| Na silicate | 5.0 | 5.0 |
| Carboxymethylcellulose | 1.0 | 1.0 |
| Methylcellulose | 0.5 | 0.5 | remainder conventional washing agent ingredients to 100%

DIN 44983 washing tests (two-liquor process, 90° C. wash, water 18° German hardness)

| | Dosage (g) pre/main wash | % Ash after 25 washing cycles | | |
|---|---|---|---|---|
| Example | | Terry towelling (Vossen) | Cotton (EMPA) | Interlock (WFK) |
| 1A | 150/150 | 2.1 | 2.3 | 2.4 |
| 1B | 150/150 | 1.2 | 0.6 | 0.6 |
| 2A | 150/150 | 2.2 | 2.4 | 2.6 |
| 2B | 150/150 | 1.3 | 0.4 | 0.4 |
| 3A | 150/150 | 1.6 | 1.4 | 1.9 |
| 3B | 150/150 | 0.3 | 0.4 | 0.6 |
| 4 | 150/150 | 3.5 | 3.3 | 3.2 |
| 5 | 150/150 | 5.9 | 5.1 | 4.8 |

DIN 44983 washing tests (two-liquor process, 60° C. wash, water 18° German hardness)

| | Dosage (g) pre/main wash | Primary cleansing action on various test fabrics (% reflectance difference) | | |
|---|---|---|---|---|
| Example | | EMPA cotton (101) | Cotton (EMPA) | WFK cotton (10 D) |
| 1A | 150/150 | 26 | 21 | 23 |
| 1B | 150/150 | 28 | 24 | 26 |
| 2A | 150/150 | 25 | 22 | 22 |
| 2B | 150/150 | 27 | 23 | 25 |
| 3A | 150/150 | 27 | 25 | 26 |
| 3B | 150/150 | 30 | 29 | 28 |
| 4 | 150/150 | 20 | 15 | 18 |
| 5 | 150/150 | 22 | 18 | 20 |

We claim:

1. A process for the preparation of a mixture of sucrose oxidation products which comprises a salt of sucrosetricarboxylic acid comprising
   reacting sucrose with oxygen in an aqueous medium in the presence of a platinum metal/active carbon catalyst at elevated temperatures; and
   neutralizing the reaction product to produce the salt of the reaction product, which comprises the starting materials being heated stepwise over the course of 5 to 15 hours from room temperature up to 60 to 95° C.

2. The process as claimed in claim 1, wherein the final temperature is 70 to 80° C.

3. The process as claimed in claim 1, wherein the temperature of the starting materials is raised, starting from room temperature, to 70 to 80° C. over the course of 8 to 12 hours by increasing the temperatures by about 1° C. about every 8 to 15 minutes.

4. The process as claimed in claim 1, further comprising isolating the reaction product.

5. The process as claimed in claim 1, wherein the catalyst is treated in an aqueous reaction medium with gaseous oxygen.

6. The process as claimed in claim 1, wherein the reaction is carried out under atmospheric pressure.

7. The process as claimed in claim 1, wherein the liquid reaction medium contains 5 to 20% by weight of sucrose.

8. The process as claimed in claim 1, wherein the oxidation is carried out at a pH of 5 to 9.

9. The process as claimed in claim 1, wherein the catalyst is a platinum/active carbon catalyst.

10. The process as claimed in claim 1, wherein the catalyst contains 5 to 10% by weight of metal.

11. The process as claimed in claim 1, wherein the salt of sucrosetricarboxylic acid is the sodium salt.

12. The process as claimed in claim 1, wherein the neutralization is carried out with an alkaline sodium compound.

13. A method of using the reaction products of claim 1, which comprises employing an effective amount of said reaction products as an essential ingredient in washing agent formulations.

14. A method of using the reaction products of claim 1, which comprises employing an effective amount of said reaction products as a food additive.

15. A washing agent containing the reaction products prepared as claimed in claim 1.

16. The process as claimed in claim 4, wherein the pH is adjusted to 8 to 10 before the isolation.

17. The process as claimed in claim 5, wherein said gaseous oxygen is highly concentrated.

18. The process as claimed in claim 8, wherein said pH is about 6 to about 8.

19. The process as claimed in claim 12, wherein said alkaline sodium compound is sodium hydroxide solution.

20. A method of using the reaction products of claim 1, which comprises employing an effective amount of said reaction products as an essential ingredient in cleaning agent formulations.

21. A cleaning agent containing the reaction products prepared as claimed in claim 1.

* * * * *